US012413583B2

(12) United States Patent
Nandwana et al.

(10) Patent No.: US 12,413,583 B2
(45) Date of Patent: *Sep. 9, 2025

(54) SYSTEM AND METHOD FOR PATIENT COMMUNICATION

(71) Applicant: Optiks Solutions, Inc., Edison, NJ (US)

(72) Inventors: Anupam Nandwana, Piscataway, NJ (US); Edward Vaz, Piscataway, NJ (US)

(73) Assignee: Optiks Solutions, Inc.

( * ) Notice: Subject to any disclaimer, the term of this patent is extended or adjusted under 35 U.S.C. 154(b) by 325 days.

This patent is subject to a terminal disclaimer.

(21) Appl. No.: 17/882,809

(22) Filed: Aug. 8, 2022

(65) Prior Publication Data

US 2023/0053829 A1 Feb. 23, 2023

Related U.S. Application Data

(60) Provisional application No. 63/234,881, filed on Aug. 19, 2021.

(51) Int. Cl.
*H04L 9/40* (2022.01)
*G16H 80/00* (2018.01)
*H04L 67/12* (2022.01)

(52) U.S. Cl.
CPC ......... *H04L 63/0861* (2013.01); *G16H 80/00* (2018.01); *H04L 67/12* (2013.01)

(58) Field of Classification Search
CPC ... H04L 63/0861; H04L 67/12; H04L 67/562; G16H 80/00; G16H 40/20; G16H 40/67; H04W 12/065; H04W 12/47; H04W 4/80
See application file for complete search history.

(56) References Cited

U.S. PATENT DOCUMENTS

| 8,055,508 B1 | 11/2011 | Leblang |
| 9,055,023 B2 | 6/2015 | Murphy |

(Continued)

FOREIGN PATENT DOCUMENTS

| WO | 2013070631 A1 | 5/2013 |
| WO | 2017070625 | 4/2017 |
| WO | 2019070822 | 4/2019 |

OTHER PUBLICATIONS

Office Action (Non-Final Rejection) dated Apr. 24, 2024 for U.S. Appl. No. 17/214,800 (pp. 1-11).

(Continued)

*Primary Examiner* — Hany S. Gadalla
(74) *Attorney, Agent, or Firm* — GRAESER ASSOCIATES INTERNATIONAL INC; Dvorah Graeser

(57) ABSTRACT

A system and method for securing authenticated patient communication through a device that is able to trigger a patient related event through a simple online communication process. The trigger(s) determined by the device are preferably controlled through a separate application, which may be controlled through a medical user computational device and/or a server. The separate application sets the one or more triggers accessible to the device and also determines one or more conditions for activating the one or more triggers. Upon detection of one or more conditions by the device, one or more triggers are activated. The medical user computational device receives a notification of the activation of the trigger. The medical user computational device may modify the trigger, the activation of the trigger or the one or more downstream actions which occur upon activation of the trigger. Such modification may occur before activation of the trigger or after activation of the trigger. The trigger causes a patient related action to be taken, for example to call the patient back on a separate telephonic device. Preferably (Continued)

erably the device features a plurality of buttons or other simple, easy to use initiators. Each initiator preferably activates a trigger.

21 Claims, 15 Drawing Sheets

(56) References Cited

U.S. PATENT DOCUMENTS

| | | | |
|---|---|---|---|
| 9,391,937 | B2 | 7/2016 | Murphy |
| 10,831,851 | B2 | 11/2020 | Sosna |
| 11,023,667 | B1 | 6/2021 | Sosna |
| 11,023,878 | B1 | 6/2021 | Hernandez |
| 2007/0255600 | A1* | 11/2007 | Cantor ............ G16H 20/10 705/3 |
| 2007/0266156 | A1 | 11/2007 | Wilkins |
| 2010/0057250 | A1* | 3/2010 | Lim ............ G16H 20/13 705/2 |
| 2011/0006876 | A1* | 1/2011 | Moberg ............ A61M 5/16831 340/3.1 |
| 2013/0064358 | A1 | 3/2013 | Nusbaum |
| 2013/0095802 | A1* | 4/2013 | Wang ............ H04W 4/029 455/414.1 |
| 2013/0304147 | A1* | 11/2013 | Aoyama ............ A61N 1/3937 455/66.1 |
| 2013/0325503 | A1 | 12/2013 | Abrahams |
| 2014/0082511 | A1* | 3/2014 | Weissberg ............ G06F 9/452 715/740 |
| 2014/0250018 | A1 | 9/2014 | Phillips |
| 2015/0134343 | A1 | 5/2015 | Kluger |
| 2015/0350148 | A1 | 12/2015 | Kenney |
| 2016/0071094 | A1 | 3/2016 | Krishnaiah |
| 2016/0210635 | A1 | 7/2016 | Alyeshmerni |
| 2016/0307176 | A1 | 10/2016 | Renke |
| 2017/0171231 | A1 | 6/2017 | Reybok, Jr. |
| 2018/0211724 | A1* | 7/2018 | Wang ............ G16H 40/20 |
| 2018/0226157 | A1 | 8/2018 | Blanshard |
| 2018/0248804 | A1 | 8/2018 | Nandy |
| 2018/0307685 | A1 | 10/2018 | Sa |
| 2018/0367495 | A1 | 12/2018 | Kim |
| 2019/0130353 | A1 | 5/2019 | Fenty, III |
| 2019/0392936 | A1* | 12/2019 | Arric ............ G16H 40/63 |
| 2020/0075147 | A1 | 3/2020 | Farhat |
| 2020/0202996 | A1 | 6/2020 | Rastogi |
| 2020/0244605 | A1 | 7/2020 | Nagaraja |
| 2020/0244615 | A1 | 7/2020 | O'Brien |
| 2020/0313910 | A1 | 10/2020 | Lindemann |
| 2020/0335209 | A1 | 10/2020 | Holscher |
| 2021/0125722 | A1* | 4/2021 | Sherkat ............ G06V 10/764 |
| 2021/0233627 | A1 | 7/2021 | Foley |
| 2021/0251562 | A1* | 8/2021 | Jain ............ G16H 50/20 |
| 2021/0304880 | A1 | 9/2021 | Nandwana |
| 2022/0384061 | A1 | 12/2022 | Nandwana |

OTHER PUBLICATIONS

International Search Report and Written Opinion issued in PCT/IB2023/55273, dated Oct. 10, 2023, 11 pages.
Notice of Allowance dated Mar. 23, 2022 for U.S. Appl. No. 16/893,474 (pp. 1-9).
Office Action (Non-Final Rejection) dated Jan. 12, 2023 for U.S. Appl. No. 17/709,703 (pp. 1-15).

* cited by examiner

End-End Flow

Figure 10 — Firmware Flow for Wi-Fi (w/ RFID) Devices

Firmware Flow for LTE-M (w/ RFID) Devices

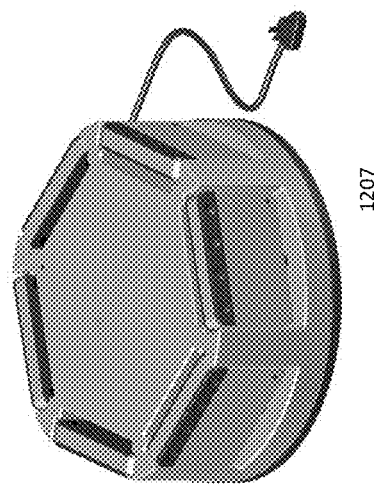
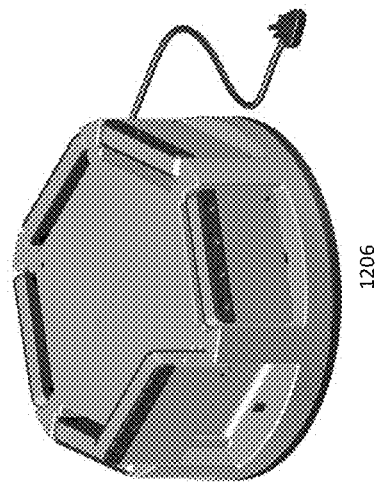
Figure 12B
Device Docking Station

Device internal flow / logic diagram

SYSTEM AND METHOD FOR PATIENT COMMUNICATION

FIELD OF THE INVENTION

The present invention is of a system and method for secure patient communication, and in particular, of such a system and method for securing authenticated patient communication through a device that is able to trigger a patient related event through a simple online communication process.

BACKGROUND OF THE INVENTION

Currently there is a significant problem for supporting simple patient communication. The ubiquity of smart phones means that potentially sophisticated communication is possible, yet such devices are inherently insecure. These devices may also be difficult for the elderly or disabled to operate. Land line telephones are limited in their functionality and also may be difficult for the elderly or disabled to operate. Devices that are simple to operate, such as for example a panic button, are also quite limited in the range of supported functions.

BRIEF SUMMARY OF THE INVENTION

The present invention overcomes the drawbacks of the background art by providing a system and method for securing authenticated patient communication through a device that is able to trigger a patient related event through a simple online communication process.

The trigger(s) determined by the device are preferably controlled through a separate application, which may be controlled through a medical user computational device and/or a server. The separate application sets the one or more triggers accessible to the device and also determines one or more conditions for activating the one or more triggers. Upon detection of one or more conditions by the device, one or more triggers are activated. The medical user computational device receives a notification of the activation of the trigger. The medical user computational device may modify the trigger, the activation of the trigger or the one or more downstream actions which occur upon activation of the trigger. Such modification may occur before activation of the trigger or after activation of the trigger. The trigger causes a patient related action to be taken, for example to call the patient back on a separate telephonic device. Preferably the device features a plurality of buttons or other simple, easy to use initiators. Each initiator preferably activates a trigger.

Implementation of the method and system of the present invention involves performing or completing certain selected tasks or steps manually, automatically, or a combination thereof. Moreover, according to actual instrumentation and equipment of preferred embodiments of the method and system of the present invention, several selected steps could be implemented by hardware or by software on any operating system of any firmware or a combination thereof. For example, as hardware, selected steps of the invention could be implemented as a chip or a circuit. As software, selected steps of the invention could be implemented as a plurality of software instructions being executed by a computer using any suitable operating system. In any case, selected steps of the method and system of the invention could be described as being performed by a data processor, such as a computing platform for executing a plurality of instructions.

Unless otherwise defined, all technical and scientific terms used herein have the same meaning as commonly understood by one of ordinary skill in the art to which this invention belongs. The materials, methods, and examples provided herein are illustrative only and not intended to be limiting.

An algorithm as described herein may refer to any series of functions, steps, one or more methods or one or more processes, for example for performing data analysis.

Implementation of the apparatuses, devices, methods and systems of the present disclosure involve performing or completing certain selected tasks or steps manually, automatically, or a combination thereof. Specifically, several selected steps can be implemented by hardware or by software on an operating system, of a firmware, and/or a combination thereof. For example, as hardware, selected steps of at least some embodiments of the disclosure can be implemented as a chip or circuit (e.g., ASIC). As software, selected steps of at least some embodiments of the disclosure can be implemented as a number of software instructions being executed by a computer (e.g., a processor of the computer) using an operating system. In any case, selected steps of methods of at least some embodiments of the disclosure can be described as being performed by a processor, such as a computing platform for executing a plurality of instructions.

Software (e.g., an application, computer instructions) which is configured to perform (or cause to be performed) certain functionality may also be referred to as a "module" for performing that functionality, and also may be referred to a "processor" for performing such functionality. Thus, processor, according to some embodiments, may be a hardware component, or, according to some embodiments, a software component.

Further to this end, in some embodiments: a processor may also be referred to as a module; in some embodiments, a processor may comprise one or more modules; in some embodiments, a module may comprise computer instructions—which can be a set of instructions, an application, software—which are operable on a computational device (e.g., a processor) to cause the computational device to conduct and/or achieve one or more specific functionality. Some embodiments are described with regard to a "computer," a "computer network," and/or a "computer operational on a computer network." It is noted that any device featuring a processor (which may be referred to as "data processor"; "pre-processor" may also be referred to as "processor") and the ability to execute one or more instructions may be described as a computer, a computational device, and a processor (e.g., see above), including but not limited to a personal computer (PC), a server, a cellular telephone, an IP telephone, a smart phone, a PDA (personal digital assistant), a thin client, a mobile communication device, a smart watch, head mounted display or other wearable that is able to communicate externally, a virtual or cloud based processor, a pager, and/or a similar device. Two or more of such devices in communication with each other may be a "computer network."

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in order to provide what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice. In the drawings:

FIGS. 12A-12C provide various non-limiting, exemplary views and flows for operation of a patient communication device according to at least some embodiments.

DESCRIPTION OF AT LEAST SOME EMBODIMENTS

Figure 1:
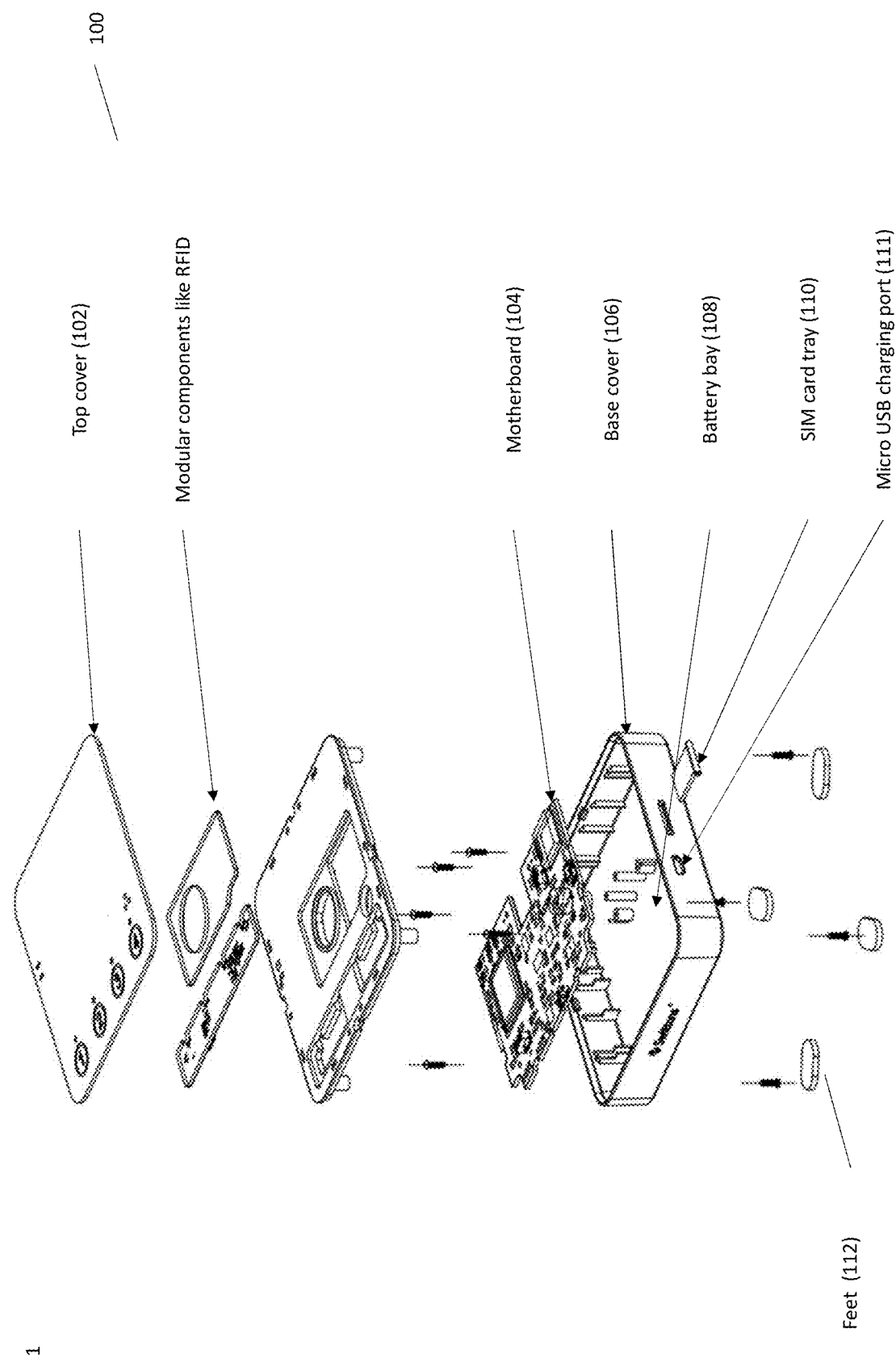
FIG. 1 shows an exemplary, non-limiting schematic diagram of a secure communication device.
Figure 2:
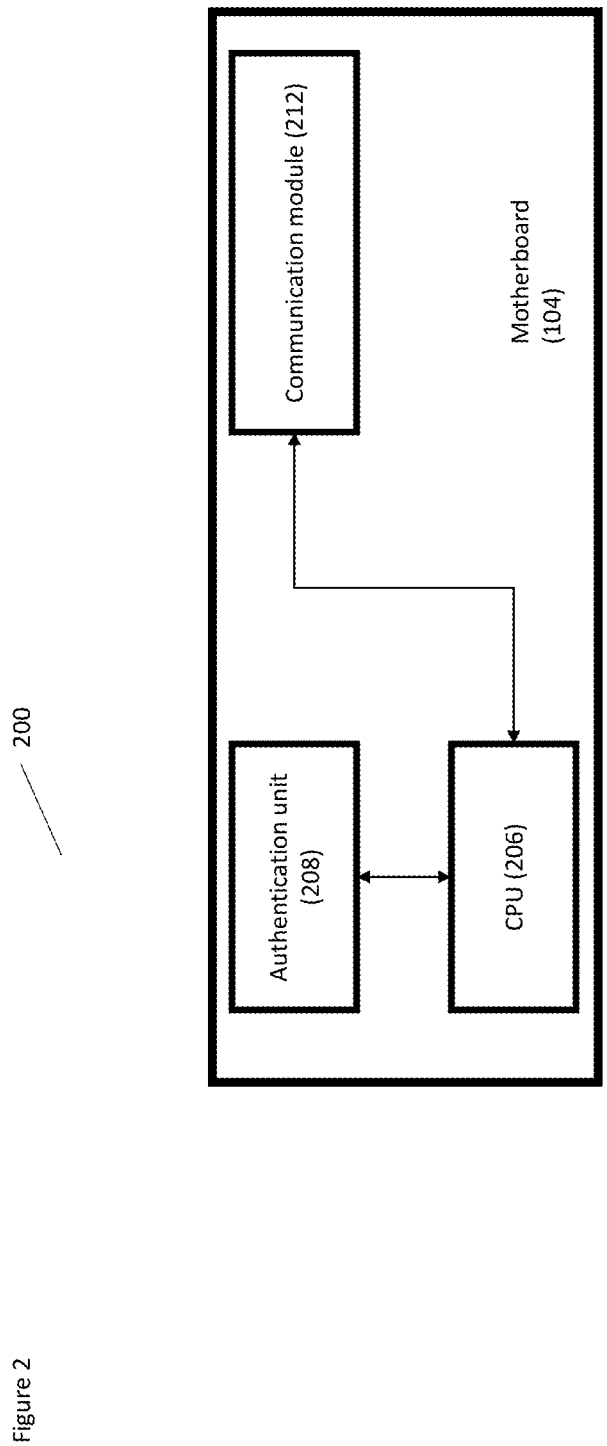
FIG. 2 shows an exemplary, non-limiting schematic diagram of the hardware components of the device of FIG. 1.

Turning now to the drawings, FIGS. 1 and 2 show exemplary, non-limiting schematic diagrams of a device for secure communication. FIG. 1 shows an exemplary, non-limiting schematic diagram of a secure communication device. As shown, a device 100 features hardware for authentication and secure communication. Device 100 comprises a top cover 102. A motherboard 104 comprises a plurality of hardware components, a non-limiting example of which is shown in FIG. 2. A bottom cover 106 preferably features sufficient room for a battery bay 108, for which a battery is shown with regard to FIG. 2.

A SIM card tray 110 is shown to permit a cellular connection, for example for a SIM card or a micro-SIM card. A charging port 111 is also provided, for example as a micro-USB port.

A plurality of feet or rubber sections 112 are preferably attached to bottom cover 106, to increase friction and hence stability for device 100.

FIG. 2 shows an exemplary, non-limiting schematic diagram of the hardware components of the device of FIG. 1. As shown with regard to hardware 200, components are arranged on motherboard 104. Power is preferably provided by a battery (not shown), which may for example comprise a power input of not more than 2000 mAh, such as a 1100 mAh power input, for example through the charging port shown in FIG. 1. A CPU 206 manages overall functionality of hardware 200. CPU 206 may for example be implemented as any suitable processing unit. Hardware 200 is turned off and on through a power switch (not shown).

Secure communication is optionally and preferably supported through an authentication unit 208, which may for example comprise RFID (radio-frequency identification) and/or biometric authentication. For example, for RFID authentication, optionally a card or other physical object is retained and manipulated by an authorized user. The card or other physical object comprises a passive or active tag. When brought into communication proximity, the RFID reader reads the RFID signal and then determines whether the card or other physical object has been authenticated to permit access, in this example to hardware 200 and hence to communication through the device of FIG. 1. Biometric authentication involves viewing a body part of a user to be authenticated, including but not limited to a fingerprint, palm print, retina, iris and the like. If present, authentication unit 208 preferably features an imager or scanner, or is in communication with same (not shown) to receive the biometric information for authentication.

Communication between authentication unit 208 and CPU 206 is preferably performed according to SPI (Serial Peripheral Interface) based communication. SPI communication features a continuous stream of data rather than packets. CPU 206 is the controlling device while authentication unit 208 receives instructions from CPU 206, and reports back with data accordingly. A clock (not shown) is used to maintain synchronization of communication between authentication unit 208 and CPU 206.

The patient or other user is preferably able to trigger one or more actions through some type of user interface. Optionally user interface hardware 210 comprises one or more of a display screen, a touchscreen, a touch button, a sound generation component or an LED. In a preferred embodiment, user interface hardware 210 comprises 4 touch buttons, 1 buzzer and 6 LEDs. This combination may be provided to support a simple interface for the user to input information, through the touch buttons, and to receive information in return, such as for example notifications, through the buzzer and LEDs combination.

The user may for example initiate communication by pressing a button as part of user interface hardware 208. CPU 206 would then instruct authentication unit 208 to receive user authentication 208. If sufficient for authentication, then CPU 206 would accept the instructions from the user in the form of the touch button push and/or other interactions with user interface hardware 210. Additionally or alternatively, CPU 206 determines authentication according to communication with another device, other than device 100, as described with regard to FIG. 3.

Hardware 200 preferably comprises a communication module 212, which may for example include cellular or WiFi connectivity as described herein. Communication module 212 may be implemented according to a BG95-M3 (or an equivalent chipset). Communications module 212 may support one or more of 2G, LTE CAT-M1, and/or may comprise multi-mode LPWA modules implemented according to Multi Mode EGPRS (enhanced GPRS (General Packet Radio Service)) for data communication. Communication between communication module 212 and CPU 206 is preferably performed according to UART (Universal Asynchronous Receiver/Transmitter) based communication, for example for the previously described authentication and/or user communication. UART communication is hardware based, through a physical circuit.

Communication module 212 may communicate with a SIM card 214, which may for example comprise a SIM card, a micro-SIM card, a NANO-SIM card or an electronic SIM card. SIM card 214 enables correct identification and authentication of hardware 200 (and hence of device 100) on the cellular network. The cellular network for example may comprise one or more of LTE-M, Cellular or NB-2. Communication module 212 may also communicate with an external antenna 216, which enables signals to be sent to and received from the cellular network, which for example may comprise one or more of LTE-M, Cellular or NB-2.

Optionally a debug port 218 is provided for hardware and/or firmware debugging.

With the exception of external antenna 216, preferably all components shown are located on motherboard 104.

Figure 3:
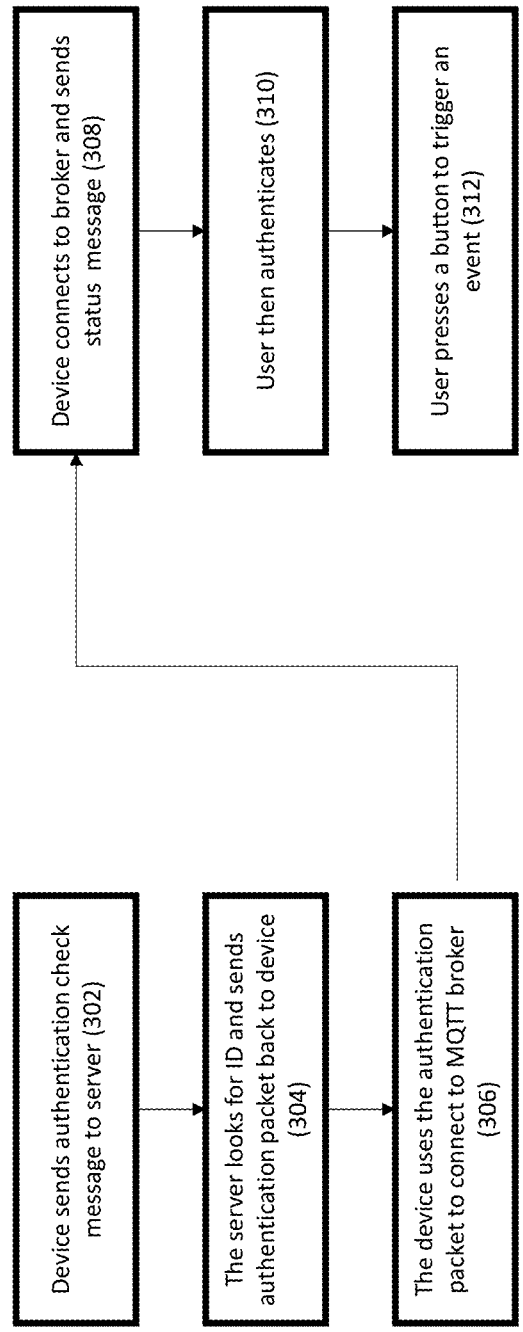
FIG. 3 shows a non-limiting exemplary flow for securely sending communication.

As shown in FIG. 3, a non-limiting exemplary flow for securely sending communication is shown, according to the device side software flow. The flow is described with regard to the device of FIGS. 1 and 2. The communication may include without limitation placing an order. An order may include but is not limited to, ordering a product or service to be provided or delivered; or causing any electronic action or set of actions to be performed. In a flow 300, steps 302-306 preferably comprise an authentication flow for authenticating the device, while steps 308-312 preferably comprise a flow for authenticating the user on that device and then permitting the event flow to occur.

At 302, the device sends authentication check message to a server. As previously described, this message is preferably initiated through some action by the user to be authenticated, for example by pressing a button on the device. The user is then authenticated as previously described, for example with an RFID card or other physical object, and/or through biometric authentication. Optionally, user authentication information is not stored on the device, such the device sends a message comprising the user's authentication information to the server.

Alternatively, user authentication occurs later in the flow, such that the device sends a request to start the authentication protocol to the server by first seeking identification of the device to the server, as part of a handshake protocol.

At 304, the server looks for ID and sends authentication packet back to the device. For example, the server preferably determines whether the received authentication information relates to an actual authenticated user. If so, then the server locates the authorized user associated with that information, in order to identify the user. The server then sends an authentication message back to the device, for example comprising an authentication packet.

Alternatively, the server looks for an identifier related to the device itself, without regard to authentication of the user at this stage. If the server finds an identifier related to the device, then it returns the authentication message back to the device. In either case, the device preferably requires receipt of this message before supporting further communication from the device.

At 306, the device uses the authentication packet to connect to MQTT broker. MQTT stands for Message Queue Telemetry Transport. An MQTT functioning component is typically implemented as a broker; a plurality of such brokers may be implemented in a cluster. MQTT is intended as a non-limiting example of an IoT communication protocol; other types of protocols could be used instead.

At 308, the MQTT broker accepts the authentication packet as part of a handshake protocol to begin communication with the device. The device then sends a status message to the broker as part of the handshake process.

If the user has not yet authenticated, then the user performs the above-described authentication process at 310. If authentication is successful, then at 312 the user presses a button to trigger an event.

Figure 4:
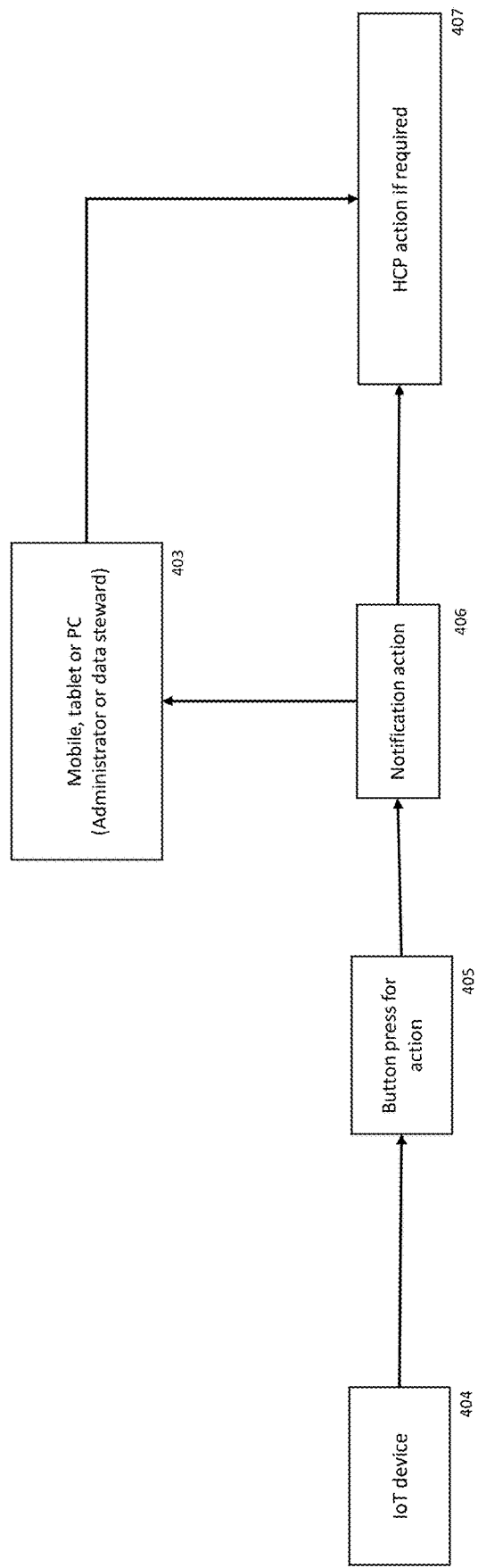
FIG. 4 shows a non-limiting exemplary flow for searching for network connectivity to enable the communication device to communicate through an external network.

FIG. 4 relates to a non-limiting exemplary end-to-end flow between a patient device and an administrative computational device. Device 404 is able to trigger an action for a patient as previously described upon authentication or at least a button push. As shown, a button press may be performed at 405 to enable the patient to communicate with the medical user computational device, for example to request a call back through a voice telephone or to indicate some other need. However, the request from the patient can be controlled, such as for example through canceling the request or rerouting the request. Preferably such control is provided through an administrator computational device 403. Computational device 403 is notified about the patient action at notification 406. In response, cancellation, modification or other types of control are shown as order modifications in 406, and are preferably performed by computational device 403. As described in greater detail below, once device 404 receives a request from the patient, notification goes to MQTT broker in the cloud (not shown). The MQTT broker then sends a notification of an event to the web application for the admin, which then notifies the computational device 403, for example. The broker may also notify medical personnel, for example through a medical user computational device, about the request from the patient. Alternatively or additionally, administrator computational device 403 may relay any such requests to a further computational device, for example in relation to medical personnel.

Figure 5:
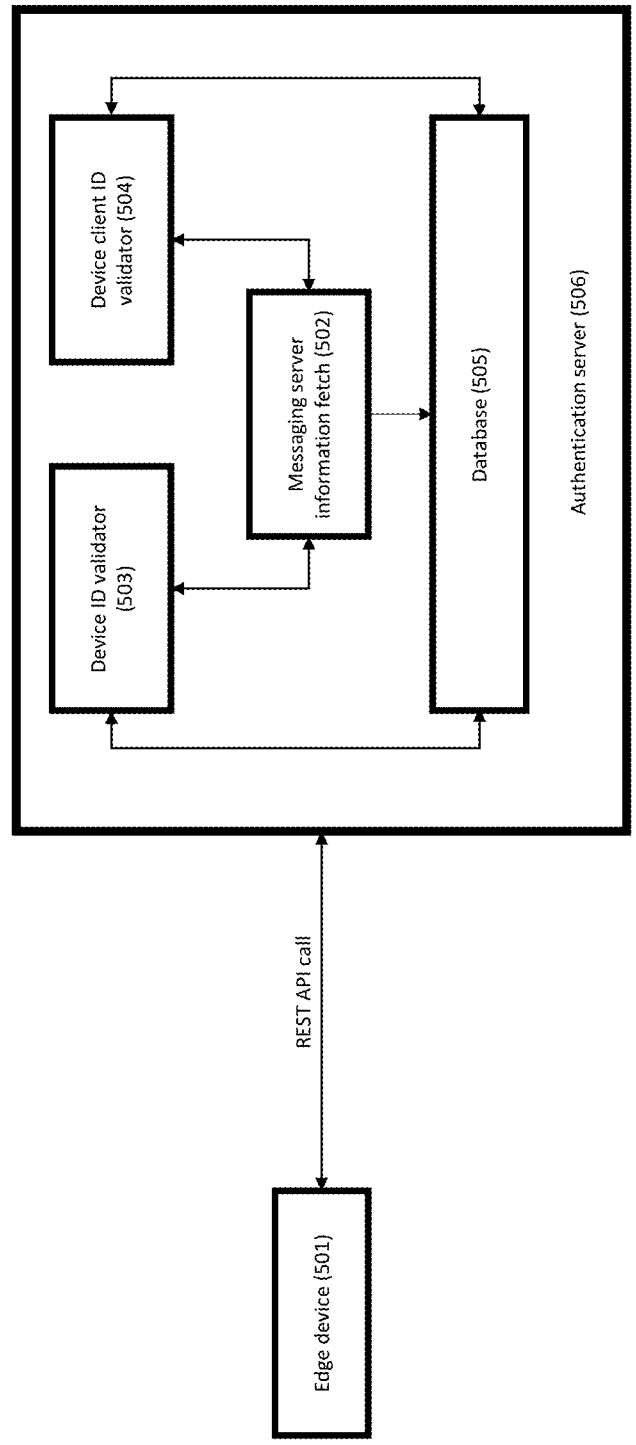
FIG. 5 shows a non-limiting exemplary flow for authentication of an edge device.

FIG. 5 shows a non-limiting exemplary flow for authentication of an edge device. As shown in a flow 500, an edge device 501 preferably triggers a REST API call to an authentication server 506, for example through the internet as previously described. Authentication server 506 receives the request and determines whether the request is valid. If the request is valid, authentication server 506 validates the request to send out the MQTT credentials from the database, such as a database 505 as shown.

For validation of the request, authentication server 506 preferably analyzes at least the identifier for edge device 501 (device ID) and also an identifier for the client (client ID). Edge device 501 is the previously described patient communication device. The client in this case may be the patient or a caregiver. Optionally and preferably both are analyzed for a complete authentication process. Alternatively, only the device ID is considered. Authentication server 506 preferably comprises a device ID validator 503 for validating the device ID, for example according to a hash and/or lookup table. Authentication server 506 preferably comprises a client ID validator 504 for validating the client ID, for example according to a hash and/or lookup table. Each of device ID validator 503 and client ID validator 504 is preferably in communication with a messaging server information fetch 502 for complete authentication and validation.

Figure 6:
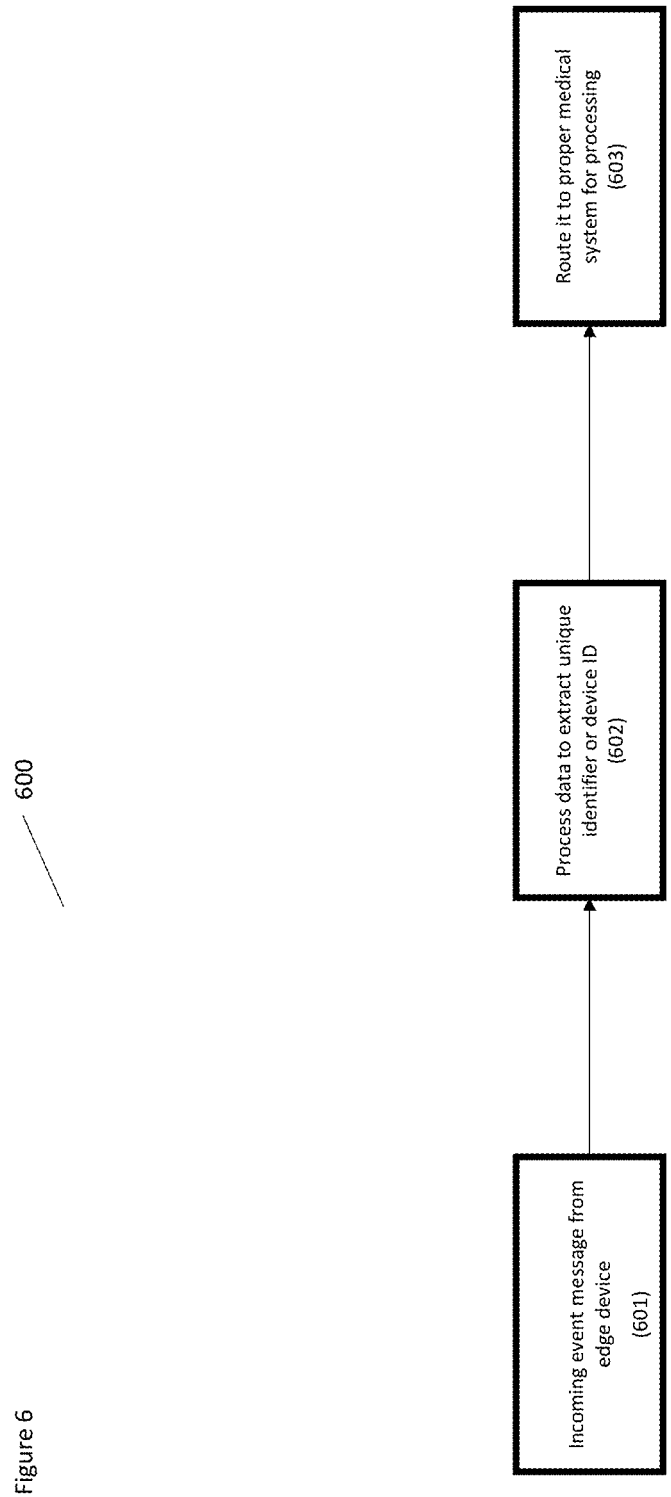
FIG. 6 shows a non-limiting exemplary flow for the routing service.

FIG. 6 shows a non-limiting exemplary flow for the routing service. The routing service may be provided as part of a routing service cluster. As shown in a flow 600, an incoming event message from an edge device is received by the routing service at 601. The edge device may be the previously described patient device for example. The routing service preferably then processes the data in the received message to extract a unique identifier or edge device ID at 602. Optionally and preferably routing is performed on a combination of the client identifier and the edge device identifier. The routing service then routes the message to the proper medical system for processing at 603. The client identifier may for example relate to a patient identifier and then the proper medical system would be the system that should receive such a triggered action from the patient, through the edge device. Such routing may occur according to an identifier which identifies the proper medical system or may occur according to the device ID. In the latter case, the device ID may specifically indicate that messages from that edge device are to be routed according to a particular medical system. Alternatively, such an indication may be provided through a lookup table that associates the device ID with a specific medical system.

Figure 7:
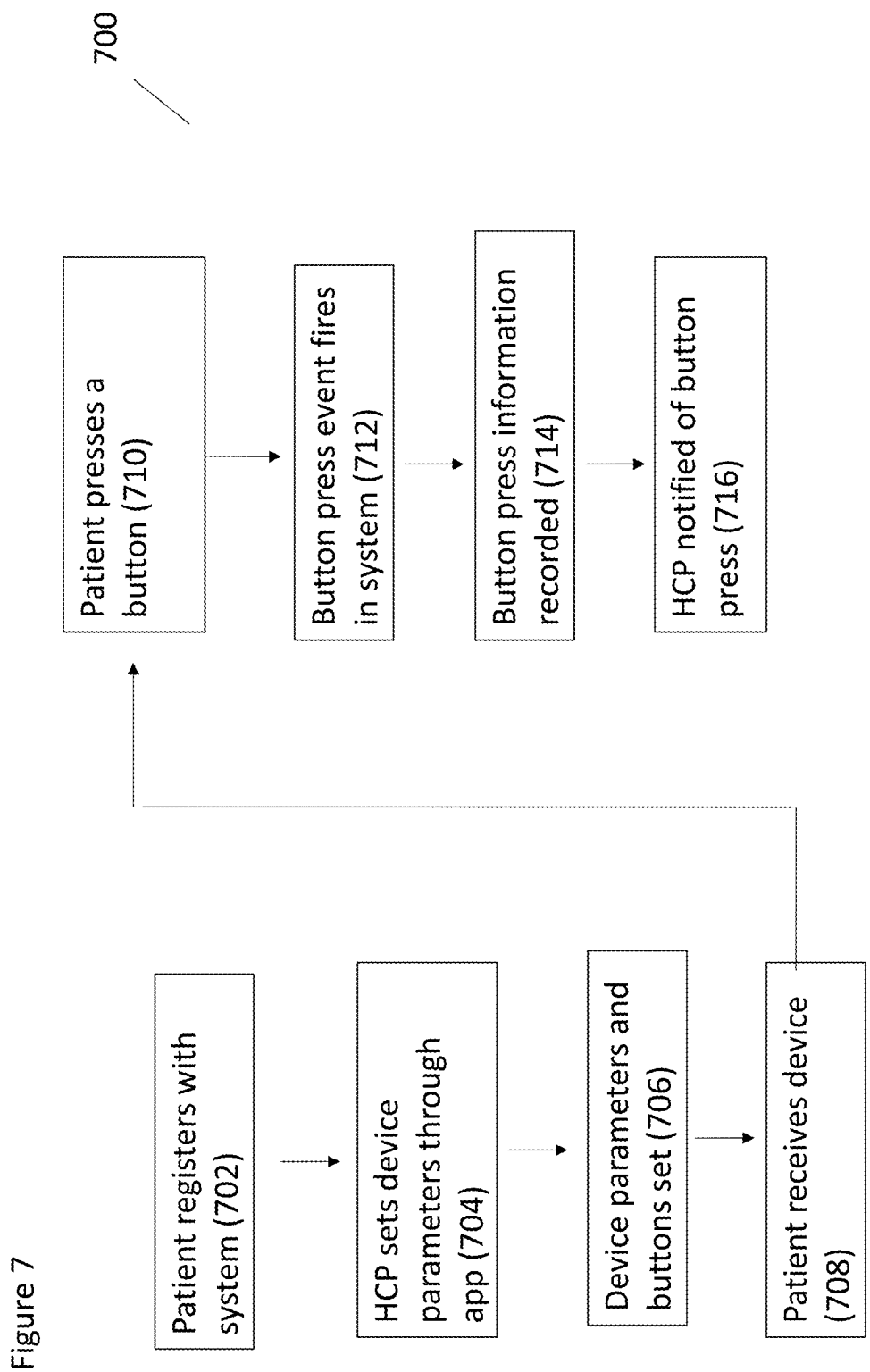
FIG. 7 shows a non-limiting, exemplary method for enabling the previously described patient device to be operated by a patient or a caregiver.

FIG. 7 shows a non-limiting, exemplary method for enabling the previously described patient device to be operated by a patient or a caregiver. A method 700 begins by having the patient register with the system at 702. The patient and/or caregiver may perform the registration process, and/or the doctor or other HCP (healthcare professional) may perform this process on behalf of the patient and/or caregiver. The HCP preferably sets device parameters through an app on the HCP computational device 704, for example to assign a trigger function to each button or other physical element of the interface on the patient device. Once these device parameters are set through the app, the device receives these settings as device parameters for actions, preferably also including button settings, at 706.

The patient and/or caregiver then receives the physical patient device at 708. Optionally device parameter settings may be transmitted remotely. The patient then presses a button and/or interacts with another physical element at 710. The button press event fires in the system at 712 and/or otherwise causes an action to be triggered within the system. The button press information is recorded and/or transmitted at 714. The HCP is then notified of the button press and/or other triggered action at 716.

Figure 8A:
FIGS. 8A and 8B show non-limiting, illustrative examples of a patient device as described herein.
Figure 8B:
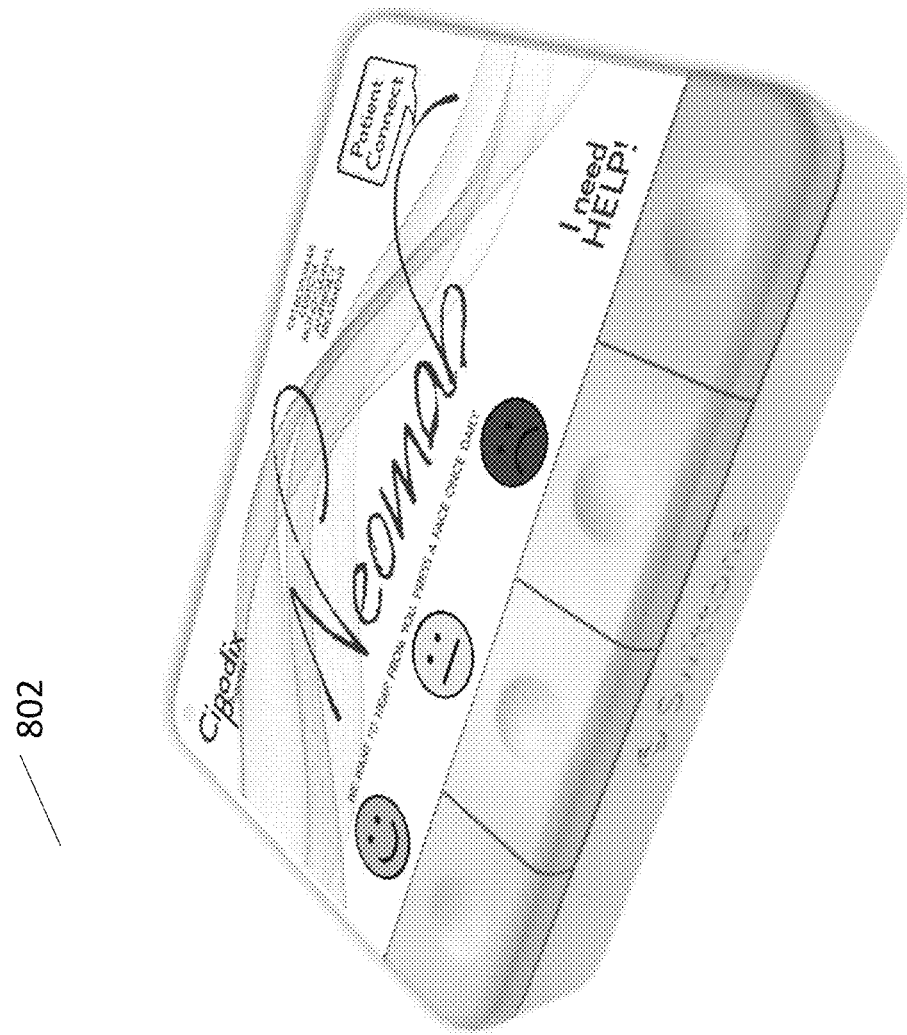

FIGS. 8A and 8B show non-limiting, illustrative examples of a patient device as described herein. FIG. 8A shows an exemplary patient concierge device 800, which may be used for example for one or more of the following: provide information on preparing for an appointment, sending appointment reminders, giving health reminders (exercise, lifestyle), enabling linkage to e-files, providing post-visit information, providing essential instruction information, giving information about doctor's phone number, address, email or other contact information; providing billing and payment status, links to logistic services, supporting Microsoft Teams/Zoom Meetings integrations and/or supporting E-Signature capabilities (Adobe, DocuSign or similar video and/or electronic signature services).

FIG. 8B shows an exemplary clinical patient engagement device 802, which may be used to communicate with a patient in a clinical trial, and also for messaging to trial physician and the company which is providing the product for the clinical trial. Clinical patient engagement device 802 may be used to do one or more of the following: providing patient "wellness" facilitation, enabling tracking of current status, providing real-time patient-reported outcomes, offering easy buttons instead of a patient portal, which also has ease of use for patient and caregivers.

Figure 9:
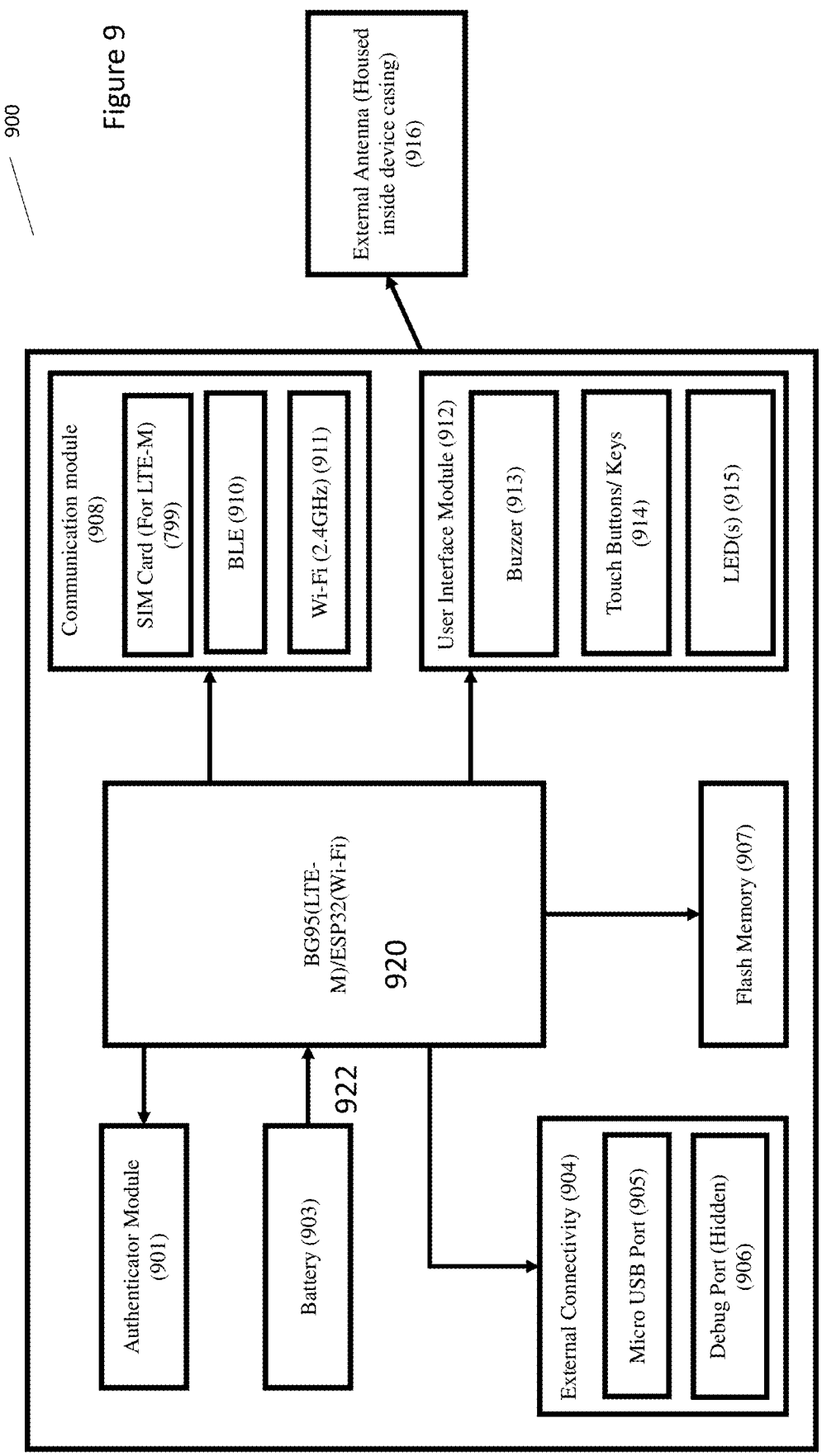
FIG. 9 shows the exemplary, non-limiting diagram of the patient device, in a non-limiting embodiment.

FIG. 9 shows the exemplary, non-limiting diagram of the patient device as described herein, in a non-limiting embodiment. As shown with regard to hardware 900, power is preferably provided by a battery 903, which may for example comprise a 1100 mAh power input, for example through the charging port shown in FIG. 1. A power distribution system 922 supplies power from battery 903 to a limited processor 920, which manages overall functionality of hardware 900. Limited processor 920 has a limited set of functions. Limited processor 920 may for example be implemented as a microcontroller unit with a communication channel, which may for example comprise a cellular modem, a WiFi modem, or a combination thereof. Limited processor 920 may for example be implemented as a BG95 (LTE-M)/ESP32. Limited processor 920 is preferably limited in that input/output capabilities are limited and also preferably only limited communication ports are supported. Limited processor 920 may for example comprise a microcontroller or a FPGA (field programmable gate array). Functions of limited processor 920 are preferably arranged such that a user is only able to interact with hardware 900 with a limited, predefined set of inputs and is only able to receive a limited, predefined set of outputs. Optionally and preferably, the limited, predefined set of inputs comprises one or more button pushes and/or an authentication input. The buttons may be physical buttons, switches, sliders, toggles and the like; and/or GUI (graphical user interface) buttons, switches, sliders, toggles and the like. The limited, predefined set of outputs optionally and preferably comprises a sound, a light or the like. Optionally, other outputs are not provided through hardware 900 but instead are provided through an external component in the associated system as described herein.

Hardware 900 is turned off and on through a power switch (not shown).

Secure communication is optionally and preferably supported through an authenticator module 901, which may for example comprise RFID (radio-frequency identification) and/or biometric authentication. For example, for RFID authentication, optionally a card or other physical object is retained and manipulated by an authorized user. The card or other physical object comprises a passive or active tag. When brought into communication proximity, the RFID reader reads the RFID signal and then determines whether the card or other physical object has been authenticated to permit access, in this example to hardware 900. Biometric authentication involves viewing a body part of a user to be authenticated, including but not limited to a fingerprint, palm print, retina, iris and the like. If present, authenticator module 901 preferably features an imager or scanner, or is in communication with same (not shown) to receive the biometric information for authentication.

Communication between authenticator module 901 and limited processor 920 is preferably performed according to SPI (Serial Peripheral Interface) based communication. SPI communication features a continuous stream of data rather than packets. Limited processor 920 is the controlling device while authenticator module 901 receives instructions from limited processor 920, and reports back with data accordingly. A clock is used to maintain synchronization of communication between authenticator module 901 and limited processor 920.

A user interface module 912 preferably supports communication of indicators to the user, including without limitation acceptance or rejection of authentication, success or failure of communication, charging status, input of communication and the like. User interface module 912 preferably communicates with limited processor 920 according to the General Purpose Input Output (GPIO) interface. Optionally user interface module 912 comprises one or more of a display screen, a touchscreen, a touch button, a sound generation component or an LED. In a preferred embodiment, user interface module 912 is limited to the previously described limited inputs and outputs, and so features only a physical and/or virtual button or other limited input 914 as described herein, a sound output 913 such as a buzzer, and a light output 915 such as a LED. In a non-limiting embodiment, user interface module 912 comprises 4 touch buttons, 1 buzzer and 6 LEDs. This combination may be provided to support a simple interface for the user to input information, through the touch buttons, and to receive information in return, such as for example notifications, through the buzzer and LEDs combination.

The user may for example initiate communication by pressing a button 914 as part of user interface module 912. Limited processor 920 would then instruct authentication module 901 to receive user authentication. If sufficient for authentication, then limited processor 920 would accept the instructions from the user in the form of the touch button push and/or other interactions with the limited input(s) of user interface module 912. Additionally or alternatively, limited processor 920 determines authentication according to communication with another external device, as described herein.

Hardware 900 preferably comprises a communication module 908, which may for example include cellular or WiFi connectivity as described herein. Communication module 908 may be implemented according to a BG95-M3, which comprises multi-mode LPWA modules implemented according to Multi Mode EGPRS (enhanced GPRS (General Packet Radio Service)) for data communication. Communication between communication module 908 and limited processor 920 is preferably performed according to UART (Universal Asynchronous Receiver/Transmitter) based communication, for example for the previously described authentication and/or user communication. UART communication is hardware based, through a physical circuit.

In this non-limiting example, communication module 908 comprises a SIM card 909, which may for example comprise a SIM card, a micro-SIM card or a NANO-SIM card. SIM card 909 enables correct identification and authentication of hardware 900 (and hence of the patient device) on the cellular network. The cellular network for example may comprise one or more of LTE-M, Cellular or NB-2. Communication module 908 may also communicate with an external antenna 918, which enables signals to be sent to and received from the cellular network, which for example may comprise one or more of LTE-M, Cellular or NB-2. External antenna 918 is preferably separate from the motherboard but is still preferably contained within the casing for the patient device (not shown).

Communication module 908 may also feature a Bluetooth module 910, which is more preferably a BLE (Bluetooth low energy module). Bluetooth module 910 may support communication with another device, which may in turn relay outgoing messages from, and send back incoming messages to, hardware 900. Bluetooth module 910 may be provided in addition to, or in place of, SIM card 909.

Communication module 708 may also feature a WiFi module 911, which may for example be a 2.4 GHz module.

Preferably, an external connectivity module 904 is provided to enable direct communication with hardware 900. Optionally a debug port 906 is provided for hardware and/or firmware debugging. Also optionally, a micro-USB port 905 is provided for powering the device, and for this embodiment, charging battery 903.

Hardware 900 also optionally and preferably features a flash memory 907. Limited processor 920 is able to write data to, and read data from, flash memory 907. Flash memory 907 may also store instructions for operation of hardware 900.

With the exception of external antenna 916, preferably all components shown are located on the motherboard.

Figure 10:
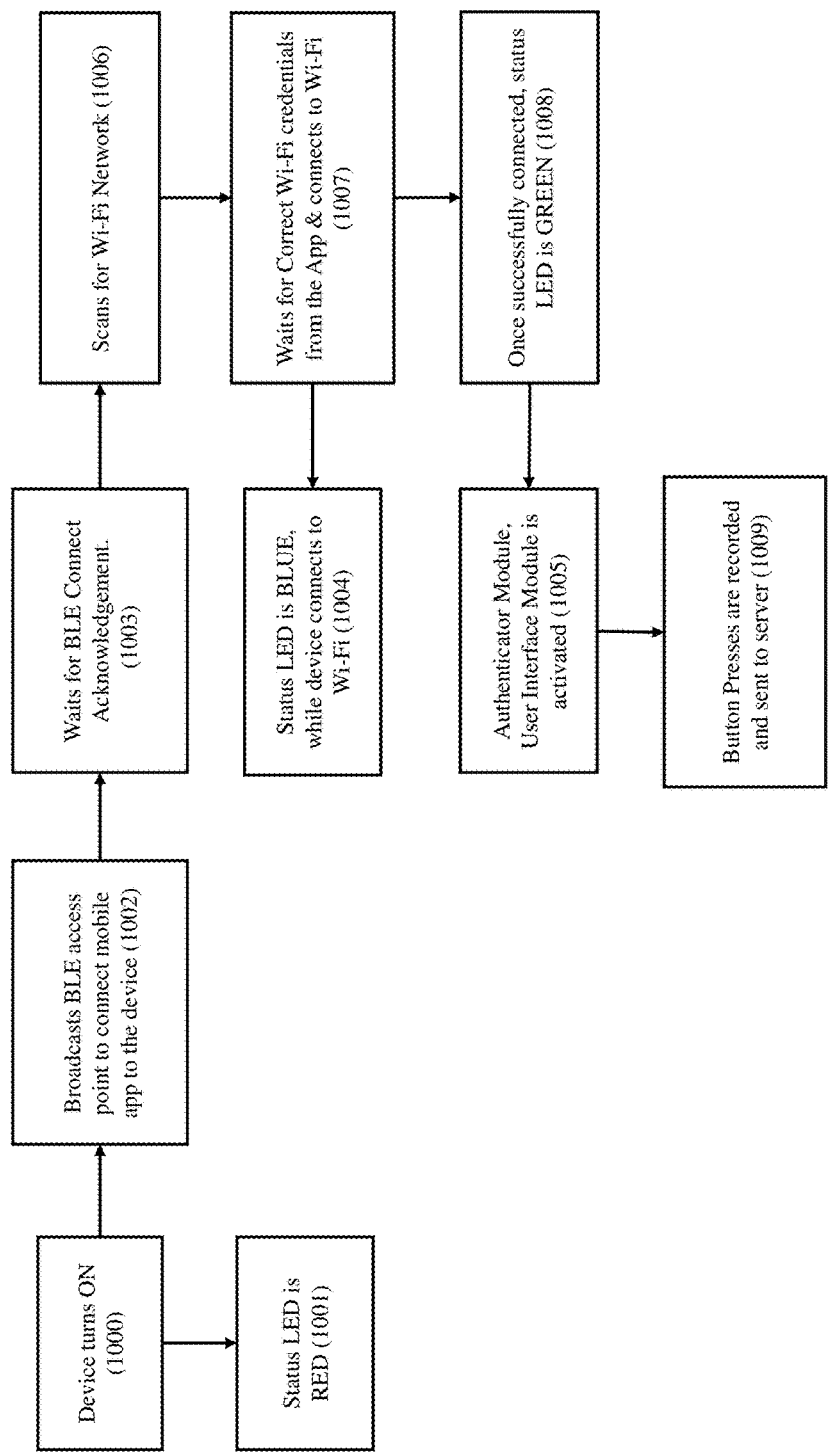
FIG. 10 shows a further non-limiting, exemplary event flow for a patient device as described herein.

FIG. 10 shows a further non-limiting, exemplary event flow for a patient device as described herein. The flow begins at 1000, when the patient communication device turns on. The device preferably shows an indication that it is not yet ready to receive instructions at 1001, for example in the form of a red LED light. The patient device then broadcasts availability of a BLE (Bluetooth low energy module) access point to connect a mobile app of an associated mobile communication device to the patient device at 1002. For devices with WiFi, the mobile app of the associated mobile communication device may be used to configure the patient device to communicate through the required network.

The patient device then waits for a BLE connect acknowledgement at 1003. The patient device then scans for a Wi-Fi Network at 1006, as preferably the patient device communicates directly with the internet through a Wi-Fi Network. Bluetooth connectivity is preferably used to support communication between the patient device and the mobile app of the associated mobile communication device, and/or another sensor or sensors. The patient device then waits for the correct Wi-Fi credentials from the mobile app, which are preferably transmitted through the previously described BLE connectivity. Upon receipt of these credentials, the patient device connects to the Wi-Fi network at 1007.

While the patient device is waiting for Wi-Fi connectivity, it may indicate a waiting status at 1004, for example with a blue LED light.

Once the patient device successfully connects to the Wi-Fi network, it preferably indicates a success status at 1008, for example with a green LED light. The authenticator module and user interface module are then preferably activated at 1005, as authentication is preferably required at this point. Once authentication has occurred, user inputs, such as button presses for example, are transmitted to the server at 1009.

Figure 11:
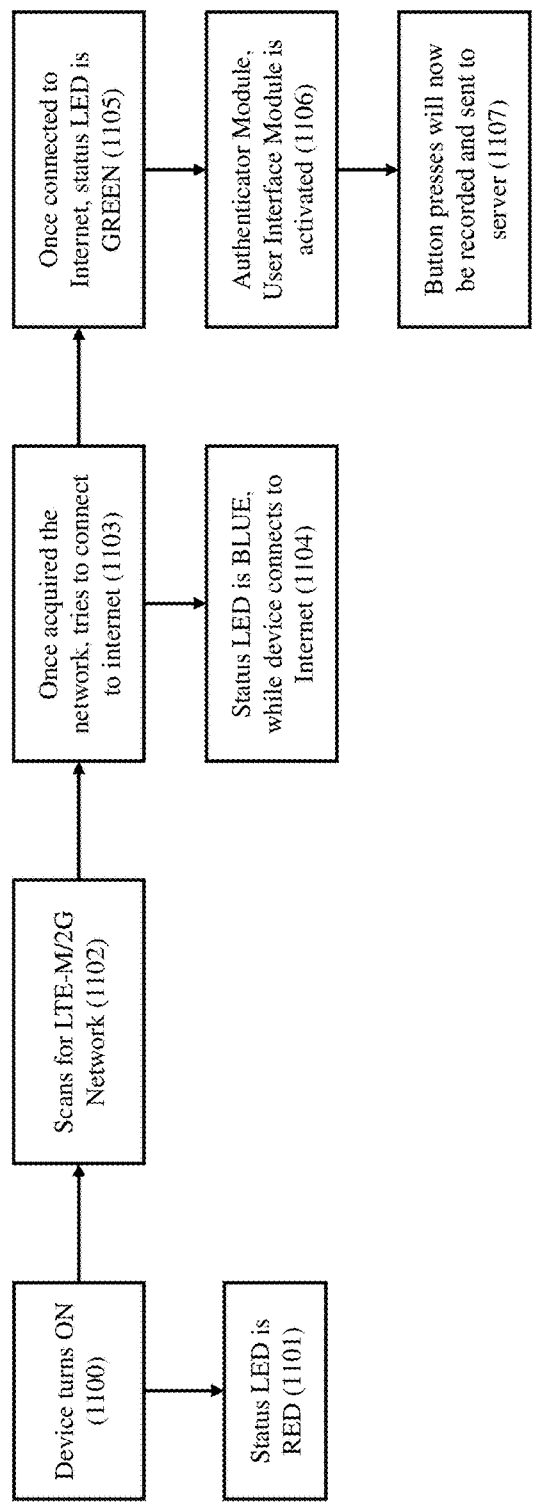
FIG. 11 shows a further non-limiting, exemplary event flow for a patient device communicating through a wireless network as described herein.

FIG. 11 shows a further non-limiting, exemplary event flow for a patient device communicating through a wireless network as described herein. The flow begins at 1100, when the IoT communication device turns on. The device preferably shows an indication that it is not yet ready to receive instructions at 1101, for example in the form of a red LED light.

Next, the patient communication device scans for a wireless network, such as the LTE-M/2G cellular network at 1102. Once the patient device acquires the wireless network connectivity, it attempts to connect to the internet at 1103. While the patient device is waiting for internet connectivity, it may indicate a waiting status at 1104, for example with a blue LED light.

Once the patient device successfully connects to the internet, it preferably indicates a success status at 1105, for example with a green LED light. The authenticator module and user interface module are then preferably activated at 1106, such that authentication is preferably required at this point. Once authentication has occurred, user inputs, such as button presses for example, are transmitted to the server at 1107.

Figure 12A:
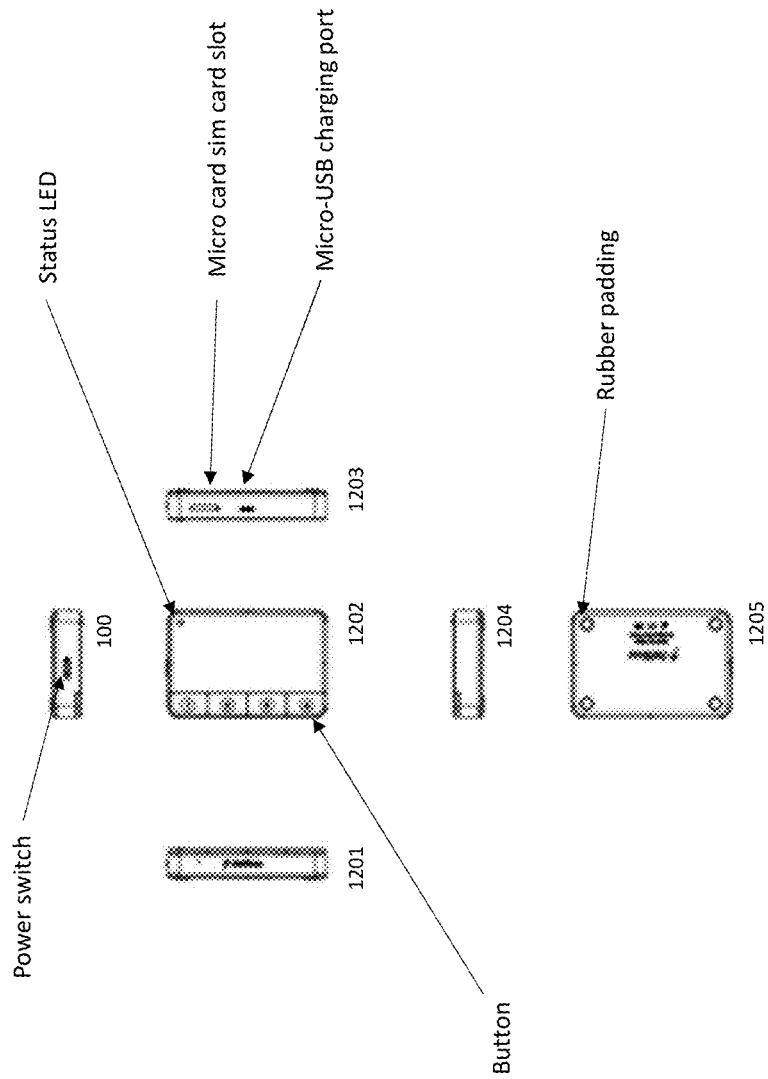

FIG. 12A shows another embodiment of a patient device as described herein. As shown in a plurality of views, a patient device 1200 features hardware for authentication that preferably does not require a fingerprint. The view at 1200 shows a power button. A side view is shown at 1201, a front-end view 1202, another side view at 1203, a view at 1204, and a back view at 1205. Front-end view 1202 includes a plurality of buttons, at least 1 and optionally up to four buttons, as well as an optional LED to indicate status. Optionally device 1200 comprises a sensor in addition to, or in place of, one or more buttons for receiving direct input for determining an action to be triggered. At 1203, a slot is shown to permit a cellular connection, for example for a SIM card or a micro-SIM card. The view at 1203 also shows a charging port. View at 1205 shows exemplary feet or rubber padding.

FIG. 12B shows a non-limiting exemplary device docking station shown in two embodiments, 1206 and 1207, for permitting the devices to dock and recharge. In view 1206, the device is showing coming into the docking station and in 1207, the device is showing as fully docked. Optionally, up to six devices 1200 are charged in the docking station.

Figure 12C:
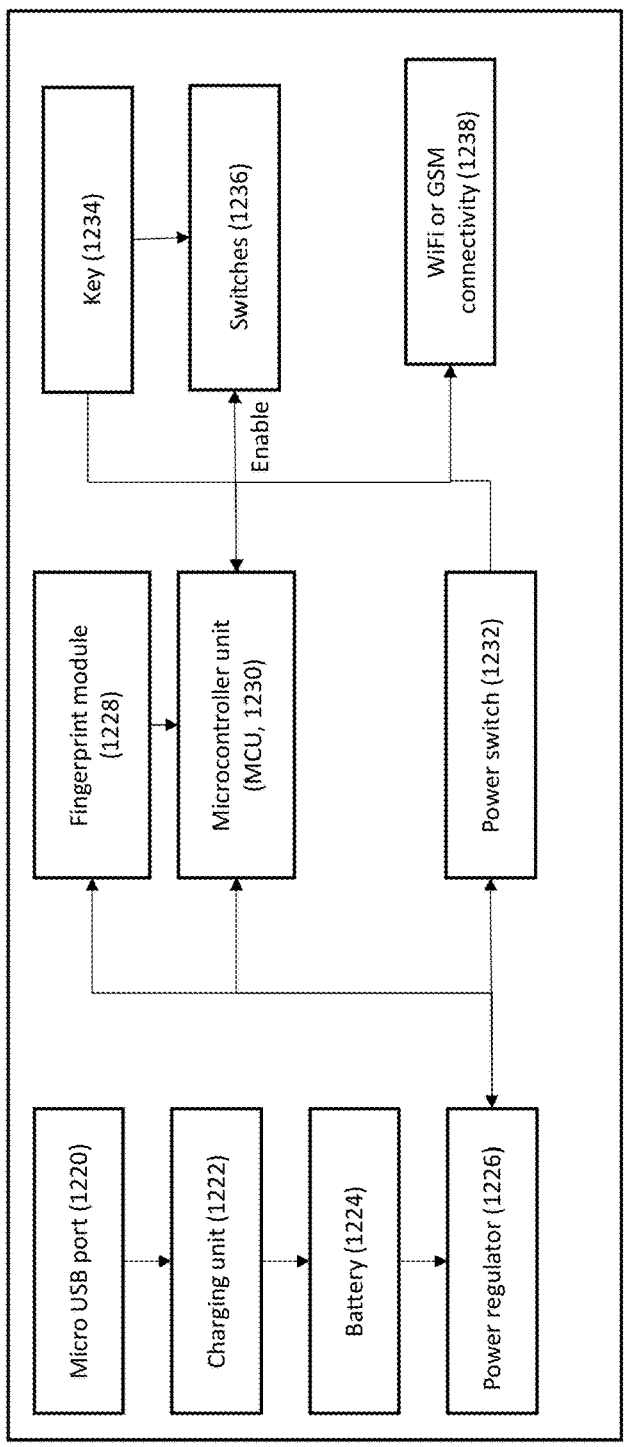

FIG. 12C shows an internal flow for the operation of the device. As shown in device 1200, power is preferably received through a micro-USB port 1220 and then flows to charging unit 1222. Charging unit 1222 then charges a battery 1224 as needed. Battery 1224 enables device 1200 to operate without being connected to the docking station as shown in FIG. 12B, or another source of power, except as needed to maintain a required charge on battery 1224.

A power regulator 1226 supplies power from battery 1224 to an optional fingerprint module 1228, for optionally identifying a user of device 1200 through a fingerprint. Power regulator 1226 also supplies power to a MCU (microcontroller unit, 1230), which manages overall functionality of device 1200. Device 1200 is turned off and on through a power switch 1232.

Power switch 1232 further controls power to a key 1234 and switches 1236. The combination of key 1234 and switch or switches 1236 forms a button as previously described, for being activated by a user through pressing the button, for example. Power switch 1232 further controls power to a connectivity module 1238, which may for example include cellular or WiFi connectivity as described herein.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A system for controlling an offline event for an authenticated patient, comprising a computer network, a patient communication device for triggering the offline event, wherein the patient communication device is controllable separately by a user, wherein the patient communication device comprises an edge device, the patient device comprising a computer network connection to the computer network, a first processor and a first memory, wherein said first memory stores a plurality of instructions for triggering the offline event and wherein said first processor executes said plurality of instructions; wherein said first processor is a limited function processor;

a server for receiving a trigger for the offline event from the edge device through the computer network; and a user computational device for receiving a notification of the trigger for the offline event from the server, wherein the user computational device is able to control the offline event and to update at least one parameter of the offline event at the server, the user computational device comprising a user interface for receiving instructions from the user and for displaying information from the server, and a computer network connection to the computer network;

wherein said edge device for triggering the offline event comprises at least one physical element for receiving a trigger input, at least one sensor for receiving a trigger input, or both; wherein said at least one physical element, said at least one sensor or both comprises a direct input for directly triggering an action;

the system further comprising a separate application, wherein said separate application is accessible through the user computational device and wherein said separate application modifies or cancels the offline event at the server according to one or more user commands entered through the user computational device and executed by the separate application at the server; wherein one or more instructions are received through said separate application for modifying the trigger; and wherein said separate application determines execution of said action that is triggered according to one or more rules, such that said execution is performed automatically upon being triggered by said at least one physical element, said at least one sensor or both, and such that said offline event is performed automatically;

wherein said edge device is registered at the server, such that the server accepts the trigger only if said edge device is registered and if a patient associated with said edge device is authenticated through said edge device, through said separate application or both;

the system further comprising a HCP (healthcare professional) computational device for receiving the trigger from the server;

wherein said physical element comprises at least one of a button, a knob, or a slider;

wherein a trigger function is assigned to said physical element through said user computational device; wherein upon patient interaction with said physical element, said patient communication device causes instructions to be sent by the edge device to the server for triggering the offline event, said instructions being determined according to said assigned trigger function.

2. The system of claim 1, wherein said user computational device comprises a second processor and a second memory, wherein said second memory stores a plurality of instructions for operating the user interface, controlling the offline event, updating the parameter at the server and receiving the notification of the trigger.

3. The system of claim 2, wherein said limited function processor has limited input/output capabilities and limited communication ports.

4. The system of claim 3, wherein said limited function processor is a microcontroller or a FPGA (field programmable gate array).

5. The system of claim 4, wherein one or more instructions are received through said user interface for modifying activation of the trigger or the offline event.

6. The system of claim 5, wherein said modification occurs before activation of the trigger or after activation of the trigger.

7. The system of claim 1, wherein said edge device comprises hardware for authentication, wherein said trigger input is permitted only after authentication.

8. The system of claim 7, wherein said hardware for authentication is selected from the group consisting of biometric hardware and RFID (radio frequency identification) hardware.

9. The system of claim 1, wherein said server comprises a third processor and a third memory, wherein said third memory stores a plurality of instructions for executing said separate application and wherein said third processor executes said plurality of instructions.

10. The system of claim 1, further comprising a separate server comprising a computer network connection to the computer network, a fourth memory and a fourth processor, wherein said fourth memory stores a plurality of instructions for executing said separate application and wherein said fourth processor executes said plurality of instructions.

11. The system of claim 1, further comprising a client server assigned to the edge device, wherein said client server further comprises a broker for handling a message from the edge device for triggering the offline event and a routing service for routing the message from the broker to said client server; wherein upon routing the message to said client server, the user computational device is notified of the message and of the triggered offline event; wherein said client server comprises a fifth memory and a fifth processor, wherein instructions for executing said broker and said routing service are stored on said fifth memory for execution by said fifth processor.

12. The system of claim 11, wherein the edge device, the broker and the routing service communicate according to the MQTT (Message Queue Telemetry Transport) protocol.

13. The system of claim 12, wherein the offline event comprises ordering a physical product through the edge device.

14. The system of claim 1, wherein said first memory is configured for storing a set of instructions and wherein said first processor is configured to perform a defined set of operations in response to receiving a corresponding instruction selected from the set of instructions stored in said first memory, wherein said set of instructions comprises instructions for receiving an input from a manual activation of at least one button; matching said input to a trigger according to one or more requirements; and invoking an event by said patient communication device to said separate application.

15. The system of claim 1, wherein said first memory is configured for storing a set of instructions and wherein said first processor is configured to perform a defined set of operations in response to receiving a corresponding instruction selected from the set of instructions stored in said first memory, wherein said set of instructions comprises receiving an input from said at least one sensor; matching said input to a trigger according to one or more requirements; and invoking an event by said patient communication device to said separate application.

16. The system of claim 15, wherein said second memory is configured for storing the set of instructions and wherein said second processor is configured to perform a defined set of operations in response to receiving a corresponding instruction selected from the set of instructions stored in said second memory, wherein said second memory stores the set of instructions comprising registering the patient communication device through said separate application; configuring said patient communication device according to one or more requirements, wherein such requirements are sent from said separate application; and invoking an event by said patient communication device through said application.

17. The system of claim 16, wherein a third memory is configured for storing the set of instructions and wherein a third processor is configured to perform a defined set of operations in response to receiving a corresponding instruction selected from the set of instructions stored in said third memory, wherein said third memory stores the set of instructions comprising accessing said separate application and invoking one or more offline events.

18. The system of claim 1, further comprising a medical user computational device for receiving a notification of activation of the trigger and for causing the offline event to be triggered.

19. The system of claim 18, wherein said medical user computational device modifies the trigger, the activation of the trigger or one or more downstream actions which occur upon activation of the trigger.

20. The system of claim 19, wherein said modification occurs before activation of the trigger or after activation of the trigger.

21. The system of claim 20, wherein activation of said trigger causes a patient related action to be taken.

* * * * *